(12) United States Patent
Gunther et al.

(10) Patent No.: US 6,432,987 B2
(45) Date of Patent: Aug. 13, 2002

(54) SUBSTITUTED N-BENZYLINDOL-3-YLGLYOXYLIC ACID DERIVATIVES HAVING ANTITUMOR ACTION

(75) Inventors: Eckhard Gunther, Maintal; Peter Emig, Bruchkobel; Dietmar Reichert, Eschau, all of (DE); Guillaume Le Baut, Saint Sebastien/Loire (FR); Bernd Nickel, Muhltal; Gerald Bacher, Heidelberg, both of (DE)

(73) Assignee: Zentaris AG, Frankfurt am Main (DE)

( * ) Notice: Subject to any disclaimer, the term of this patent is extended or adjusted under 35 U.S.C. 154(b) by 0 days.

(21) Appl. No.: 09/736,431

(22) Filed: Dec. 15, 2000

(30) Foreign Application Priority Data

Dec. 23, 1999 (DE) ......................... 199 62 300

(51) Int. Cl.$^7$ ............................................. A01N 43/40
(52) U.S. Cl. ......................................................... 514/339
(58) Field of Search ........................ 546/277.1; 514/339, 514/340

(56) References Cited

U.S. PATENT DOCUMENTS 6,008,231 A * 12/1999 Lebaut et al. ................ 514/314
6,251,923 B1 * 6/2001 Hofgen et al. ............... 514/339

FOREIGN PATENT DOCUMENTS

WO 99/55696 * 11/1999

* cited by examiner

Primary Examiner—Alan L. Rotman
(74) Attorney, Agent, or Firm—Pillsbury Winthrop LLP

(57) ABSTRACT

The invention relates to novel, substituted N-benzyl-indol-3-ylglyoxylic acid derivatives of the following formula and their use for the treatment of oncoses

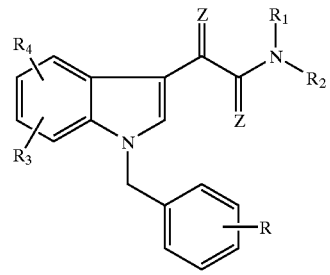

The invention further relates to their physiologically tolerable acid addition salts and if possible their N-oxides. In addition, the invention relates to pharmaceutical preparations containing at least one of the compounds of the abovementioned formula or their salts or N-oxides with physiologically tolerable inorganic or organic acids and, if appropriate, pharmaceutically utilizable vehicles and/or diluents or excipients and also administration forms of the compounds of the abovementioned formula containing at least one of the compounds of this formula or their salts in the form of tablets, coated tablets, capsules, solutions for infusion or ampoules, suppositories, patches, powder preparations which can be employed by inhalation, suspensions, creams and ointments

10 Claims, No Drawings

SUBSTITUTED N-BENZYLINDOL-3-YLGLYOXYLIC ACID DERIVATIVES HAVING ANTITUMOR ACTION

BACKGROUND OF THE INVENTION

1. Field of the Invention

The invention relates to novel N-substituted indole-3-glyoxylamides, processes for their preparation and pharmaceutical uses. The compounds according to the invention have antitumor properties.

Indole-3-glyoxylamides have a variety of uses as pharmacodynamically active compounds and as synthetic building blocks in pharmaceutical chemistry.

In the patent application Neth. Appl. 6502481, compounds are described which have an antiinflammatory and antipyretic activity profile and analgesic activity.

In the British Application GB-B 1 028 812, derivatives of indolyl-3-glyoxylic acid and their amides are mentioned as analgesic, anticonvulsant and β-adrenergic compounds.

G. Domschke et al. (Ber. 94, 2353 (1961)) describes [sic] 3-indolylglyoxylamides which are not characterized pharmacologically.

E. Walton reports in J. Med. Chem., 11, 1252 (1968) on indolyl-3-glyoxylic acid derivatives which have an inhibitory action on glycerophosphate dehydrogenase and lactate dehydrogenase.

In the European Patent Specification EP 675110, 1H-indole-3-glyoxylamides are described which are profiled as sPLA2 inhibitors and are used in the treatment of septic shock, in pancreatitis and in the treatment of allergic rhinitis and rheumatoid arthritis.

It has already been proposed in the German Patent Application having the file reference 19814838.0 to employ the compounds according to DE-A 196 36 150 A1 as antitumor agents.

DETAILED DESCRIPTION OF THE INVENTION

The aim of the present invention is to make available novel compounds from the indol-3-ylglyoxylic acid series of the general formula 1 which have a good antitumor action and can be employed for the preparation of antitumor agents;

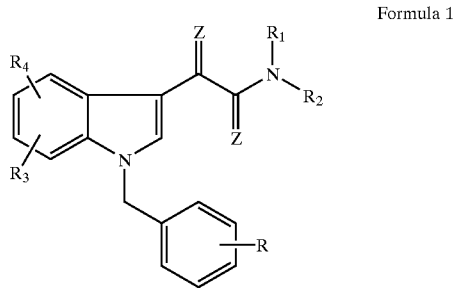

Formula 1

Where the radicals R, $R_1$, $R_2$, $R_3$, $R_4$ and Z have the following meaning R=nitro, amino, mono- or di($C_1$–$C_6$)-alkylamino, mono- or di ($C_1$–$C_6$)-cycloalkylamino, ($C_1$–$C_6$)-acylamino, phenyl ($C_1$–$C_6$)-alkylamino, aroylamino, heteroaroylamino, ($C_1$–$C_6$)-alkylsulfonamido, arylsulfonamido, maleimido, succinimido, phthalimido, benzyloxycarbonylamino (Z-amino), tert-butoxycarbonylamino (BOC-amino), 9-fluorenylmethoxycarbonylamino (Fmoc-amino), triphenylmethylamino (Tr-amino), 2-(4'-pyridyl)ethoxycarbonylamino (Pyoc-amino), diphenylmethylsilylamino (DPMS-amino), where the radicals for R can alternatively be substituted on the C atoms 2, 3 and 4 of the phenyl ring, R can furthermore be, in the case in which $R_1$=hydrogen, the methyl or phenylmethyl group and the benzyloxycarbonyl radical (Z radical), the tert-butoxycarbonyl radical (BOC radical) and the acetyl group, the following radicals: —NH—$CH_2$–COOH; —NH—CH($CH_3$)—COOH; ($CH_3$)$_2$CH—$CH_2$—$CH_2$—CH(NH)—COOH; $H_3$C—$CH_2$—CH($CH_3$)—CH(NH)—COOH; HO$H_2$C—CH(NH)—COOH; phenyl-$CH_2$—CH(NH)—COOH; (4-imidazoyl)—$CH_2$—CH(NH)—COOH; HN=C($NH_2$)—NH—($CH_2$)$_3$—CH(NH)—COOH; $H_2$N—($CH_2$)$_4$—CH(NH)—COOH; $H_2$N—CO—$CH_2$—CH(NH)—COOH; HOOC—($CH_2$)$_2$—CH(NH)—COOH $R_1$=hydrogen, ($C_1$–$C_6$)-alkyl, where the alkyl group can be mono- or polysubstituted by the phenyl ring and this phenyl ring for its part can be mono- or polysubstituted by halogen, ($C_1$–$C_6$)-alkyl, ($C_3$–$C_7$)-cycloalkyl, by carboxyl groups, carboxyl groups esterified with $C_1$–$C_6$-alkanols, trifluoromethyl groups, hydroxyl groups, methoxy groups, ethoxy groups, benzyloxy groups and by a benzyl group which is mono- or polysubstituted in the phenyl moiety by ($C_1$–$C_6$)-alkyl groups, halogen atoms or trifluoromethyl groups, $R_1$ is further the benzyloxycarbonyl group (Z group) and the tertiary-butoxycarbonyl radical (Boc radical), furthermore the acetyl group.

$R_2$ can be the phenyl ring, which is mono- or polysubstituted by ($C_1$–$C_6$)-alkyl, ($C_1$–$C_6$)-alkoxy, cyano, halogen, trifluoromethyl, hydroxyl, benzyloxy, nitro, amino, ($C_1$–$C_6$)-alkylamino, ($C_1$–$C_6$)-alkoxycarbonylamino and by the carboxyl group or by the carboxyl group esterified with $C_1$–$C_6$-alkanols, or can be a pyridine structure of the formula 2

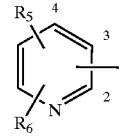

Formula 2 and its N-oxide, where the pyridine structure is alternatively bonded to the ring carbon atoms 2, 3 and 4 and can be substituted by the substituents $R_5$ and $R_6$. The radicals $R_5$ and $R_6$ can be identical or different and have the meaning ($C_1$–$C_6$)-alkyl and the meaning ($C_3$–$C_7$)-cycloalkyl, ($C_1$–$C_6$)-alkoxy, nitro, amino, hydroxyl, halogen and trifluoromethyl and further are the ethoxycarbonylamino radical and the group carboxyalkyloxy in which the alkyl group can have 1–4 C atoms.

$R_2$ can further be a 2- or 4-pyrimidinyl heterocycle, where the 2-pyrimidinyl ring can be mono- or polysubstituted by the methyl group, furthermore can be the 2-, 3-, 4-, 5-, 6-, 7- and 8-quinolyl structure substituted by ($C_1$–$C_6$)-alkyl, halogen, the nitro group, the amino group and the (C1–$C_6$)-alkylamino radical, can be a 2-, 3- and [sic] 4-quinolylmethyl group, where the ring carbons of the pyridylmethyl radical of the quinolyl group and of the quinolylmethyl radical can be substituted by ($C_1$–$C_6$)-alkyl, ($C_1$–$C_6$)-alkoxy, nitro, amino and ($C_1$–$C_6$)-alkoxycarbonylamino.

R$_2$ in the case in which R$_1$=hydrogen, the methyl or benzyl group and the benzyloxycarbonyl radical (Z radical), the tert-butoxycarbonyl radical (BOC radical) and the acetyl group can furthermore be the following radicals:

—CH$_2$COOH; —CH(CH$_3$)—COOH; (CH$_3$)$_2$CH—(CH$_2$)$_2$—CH(COOH)—; H$_3$C—H$_2$C—CH(CH$_3$)—CH(COOH)—; [HO—H$_2$C—CH(COOH)—; phenyl—CH$_2$—CH(COOH)—; (4-imidazolyl)—CH$_2$—CH(COOH)—; [HN=C(NH$_2$)—NH—(CH$_2$)$_3$—CH(COOH)—; H$_2$N—(CH$_2$)$_4$—CH(COOH)—; H$_2$N—CO—CH$_2$—CH—(COOH)—; HOOC—(CH$_2$)$_2$—CH(COOH)—;

R$_2$ in the case in which R$_1$ are [sic] hydrogen, the Z group, the BOC radical, the acetyl or the benzyl group can furthermore be the acid radical of a natural or unnatural amino acid, e.g. the α-glycyl, the α-sarcosyl, the α-alanyl, the α-leucyl, the α-isoleucyl, the α-seryl, the α-phenylalanyl, the α-histidyl, the α-prolyl, the α-arginyl, the α-lysyl, the α-asparagyl and the α-glutamyl radical, where the amino groups of the respective amino acids can be present unprotected or can be protected. A possible protective group of the amino function is the carbobenzoxy radical (Z radical) and the tert-butoxycarbonyl radical (BOC radical) as well as the acetyl group. In the case of the asparagyl and glutamyl radical claimed for R$_2$, the second, unbonded carboxyl group is present as a free carboxyl group or in the form of a carboxyl group esterified with C$_1$–C$_6$-alkanols, e.g. as a methyl, ethyl or as a tert-butyl ester. Furthermore, R$_2$ can be the allylaminocarbonyl-2-methylprop-1-yl group. R$_1$ and R$_2$ can further form, together with the nitrogen atom to which they are bonded, a piperazine ring of the formula 3 or a homopiperazine ring, provided R$_2$ is an aminoalkylene group, in which Formula 3

R$_7$ is an alkyl radical, is a phenyl ring which can be mono- or polysubstituted by (C$_1$–C$_6$)-alkyl, (C$_1$–C$_6$)-alkoxy, halogen, the nitro group, the amino function and by the (C$_1$–C$_6$)-alkylamino group. R$_7$ is furthermore the benzhydryl group and the bis-p-fluorobenzhydryl group.

R$_3$ and R$_4$ can be identical or different and are hydrogen, (C$_1$–C$_6$)-alkyl, (C$_3$–C$_7$)-cycloalkyl, (C$_1$–C$_6$)-alkanoyl, (C$_1$–C$_6$)-alkoxy, halogen and benzyloxy. R$_3$ and R$_4$ can furthermore be the nitro group, the amino group, the (C$_1$–C$_4$)-mono- or dialkyl-substituted amino group, and the (C$_1$–C$_6$)-alkoxycarbonylamino function or (C$_1$–C$_6$)-alkoxycarbonylamino- (C$_1$–C$_6$)-alkyl function.

Z is O and S.

The designation alkyl, alkanol, alkoxy or alkylamino group for the radicals R, R$_1$, R$_2$, R$_3$, R$_4$, R$_5$, R$_6$, R$_7$ is normally understood as meaning both "straight-chain" and "branched" alkyl groups, where "straight-chain alkyl groups" can be, for example, radicals such as methyl, ethyl, n-propyl, n-butyl, n-pentyl, n-hexyl and "branched alkyl groups" designate, for example, radicals such as isopropyl or tert-butyl. "Cycloalkyl" is understood as meaning radicals such as, for example, cyclopropyl, cyclobutyl, cyclopentyl, cyclohexyl or cycloheptyl. The designation "halogen" represents fluorine, chlorine, bromine or iodine. The designation "alkoxy group" represents radicals such as, for example, methoxy, ethoxy, propoxy, butoxy, isopropoxy, isobutoxy or pentoxy. The designation acyl of the acylamino radicals is to be understood as meaning the groups formyl, acetyl, propionyl, butyryl, valeryl and isovaleryl. The designation aroyl of the aroylamino groups represents benzoyl, naphthoyl, toluoyl, phthaloyl and the group heteroaroyl of the heteroaroylamino radicals represents nicotinoyl, isonicotinoyl, thenoyl and furoyl. The designation aryl of the arylsulfonamido group is understood as meaning phenyl, tolyl and naphthyl.

The compounds can also be employed as acid addition salts, for example as salts of mineral acids, such as, for example, hydrochloric acid, sulfuric acid, phosphoric acid, salts of organic acids, such as, for example, acetic acid, lactic acid, malonic acid, maleic acid, fumaric acid, gluconic acid, glucuronic acid, citric acid, ascorbic acid, embonic acid, methanesulfonic acid, trifluoroacetic acid, succinic acid, 2-hydroxyethanesulfonic acid, nicotinic acid and p-toluenesulfonic acid.

Both the compounds of the formula 1 and their salts are biologically active. The compounds of the formula 1 can be administered in free form or as salts with physiologically tolerable acids.

Administration can be performed orally, parenterally, intravenously, transdermally or by inhalation.

The invention furthermore relates to pharmaceutical preparations which contain at least one of the compounds of the formula 1 or their salts with physiologically tolerable inorganic or organic acids and, if appropriate, pharmaceutically utilizable excipients and/or diluents or auxiliaries.

Suitable administration forms are, for example, tablets, coated tablets, capsules, solutions for infusion or ampoules, suppositories, patches, powder preparations which can be employed by inhalation, suspensions, creams and ointments.

The processes for the preparation of the compounds according to the invention are described in the following reaction schemes 1 and 2 (Stages 1–3) and in general procedures. All compounds can be prepared as described or analogously.

The compounds of the general formula 1 with Z=O, R=NO$_2$ and NH$_2$ and R$_2$=aryl, aralkyl and heteroaryl are obtainable according to the following Scheme 1:

Scheme 1

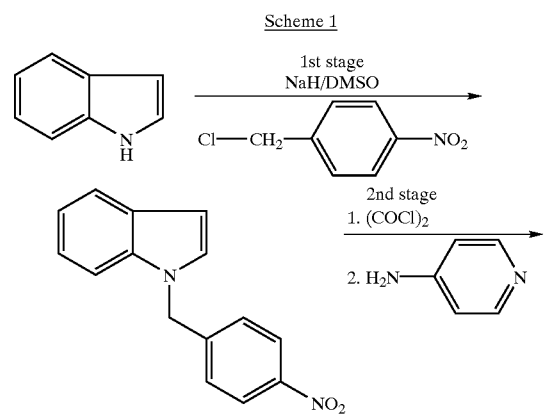

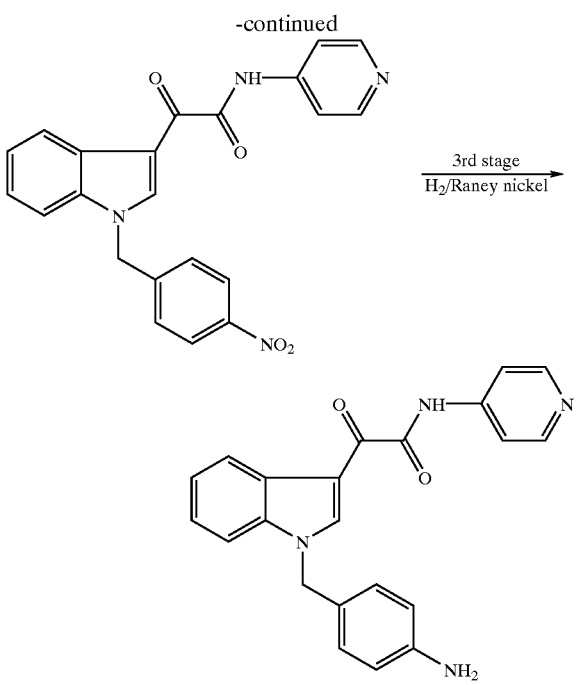

1st Stage:

The indole derivative, which can be unsubstituted or monosubstituted or polysubstituted on C-2 or in the phenyl structure, is dissolved in a protic, dipolar aprotic or nonpolar organic solvent, such as, for example, isopropanol, tetrahydrofuran, dimethyl sulfoxide, dimethylformamide, dimethylacetamide, N-methylpyrrolidone, dioxane, toluene or methylene chloride and added dropwise to a suspension of a base prepared in a three-necked flask under an $N_2$ atmosphere or employed in a molar amount or in excess, such as, for example, sodium hydride, powdered potassium hydroxide, potassium tert-butoxide, dimethylaminopyridine or sodium amide, in a suitable solvent. Then the desired alkyl, aralkyl or heteroaralkyl halide, for example, is added, if appropriate with addition of a catalyst, such as, for example, copper and the mixture is allowed to react for some time, for example for 30 minutes to 12 hours, and the temperature is maintained within a range from 0° C. to 120° C., preferably between 30° C. to [sic] 80° C., particularly between 50° C. and 65° C. After completion of the reaction, the reaction mixture is added to water, the solution is extracted, e.g. with diethyl ether, dichloromethane, chloroform, methyl tert-butyl ether or tetrahydrofuran, and the organic phase obtained in each case is dried with anhydrous sodium sulfate. The organic phase is concentrated in vacuo, the residue which remains is crystallized by trituration or the oily residue is purified by recrystallization, distillation or by column or flash chromatography on silica gel or alumina. The eluent used is, for example, a mixture of dichloromethane and diethyl ether in the ratio 8:2 (vol/vol) or a mixture of dichloromethane and ethanol in the ratio 9:1 (vol/vol).

2nd Stage

The N-substituted indole obtained according to the above procedure of the 1st stage is dissolved under a nitrogen atmosphere in an aprotic or nonpolar organic solvent, such as, for example, diethyl ether, methyl tert-butyl ether, tetrahydrofuran, dioxane, toluene, xylene, methylene chloride or chloroform and added to a solution prepared under a nitrogen atmosphere of a monomolar up to 60% excess amount of oxalyl chloride in an aprotic or nonpolar solvent, such as, for example, in diethyl ether, methyl tert-butyl ether, tetrahydrofuran, dioxane, toluene, xylene, methylene chloride, the temperature being kept between −5° C. and 20° C. The reaction solution is then heated at a temperature between 10° C. and 130° C., preferably between 20° C. and 80° C., particularly between 30° C. and 50° C., for a period of 30 minutes to 5 hours and the solvent is then evaporated. The residue of the "indolyl-3-glyoxyloyl chloride" formed in this manner which remains is dissolved in an aprotic solvent such as, for example, tetrahydrofuran, dioxane, diethyl ether, toluene or alternatively in a dipolar aprotic solvent, such as, for example, dimethylformamide, dimethylacetamide or dimethyl sulfoxide, cooled to a temperature between 10° C. and −15° C., preferably between −5° C. and 0° C., and treated in the presence of an acid scavenger with a solution of the primary or secondary amine in a diluent. Possible diluents are the solvents used above for dissolving the indolyl-3-glyoxyloyl chloride. Acid scavengers used are triethylamine, pyridine, dimethylaminopyridine, basic ion exchanger, sodium carbonate, potassium carbonate, powdered potassium hydroxide and excess primary or secondary amine employed for the reaction. The reaction takes place at a temperature from 0° C. to 120° C., preferably at 20–80° C., particularly between 40° C. and 60° C. After a reaction time of 1–3 hours and standing at room temperature for 24 hours, the hydrochloride of the acid scavenger is filtered, the filtrate is concentrated in vacuo and the residue is recrystallized from an organic solvent or purified by column chromatography on silica gel or alumina. The eluent used is, for example, a mixture of dichloromethane and ethanol (95:5, vol/vol).

3rd Stage

The N-nitrobenzyl-substituted "indoleglyoxylamide" obtained according to the above procedure (2nd stage) is dissolved in a protic solvent, such as, for example, methanol, ethanol, propanol, isopropanol or butanol or in a nonpolar solvent, such as, for example, tetrahydrofuran, dioxane or glycol dimethyl ether or in a dipolar aprotic solvent, such as, for example, dimethyl sulfoxide, dimethylformamide, dimethyl-acetamide or N-methylpyrrolidone and the solution is treated with a hydrogenation catalyst such as, for example, Raney nickel, palladium/carbon or platinum under a nitrogen atmosphere and with stirring. Hydrogen is passed into the suspension with moderate shaking at a gas pressure of 1–15 bar, preferably 2–10 bar, particularly at 4–6 bar and the temperature is raised to about 20°–80° C., preferably 30°–60° C., particularly to 45°–55° C. If appropriate, after about 1 hour a further amount of catalyst is added and the hydrogenation is continued. The hydrogenation was complete after a reaction time of 4–10 hours. The catalyst was filtered off under a nitrogen atmosphere, the solvent was concentrated to dryness in vacuo and the colorless to yellowish residue was dried in vacuo at 40° C.

Working Examples

According to this general procedure for stages 1–3, on which synthesis scheme 1 is based, the following compounds were synthesized which are evident from the following tabulated list [sic] detailing the respective chemical name.

Example 1

N-(Pyridin-4-yl)-[1-(4-aminobenzyl)indol-3-yl]glyoxyl-amide (D-68838)

1st Stage

1-(4-Nitrobenzyl)indole

A mixture of 5.28 g of sodium hydride (0.22 mol, mineral oil suspension) in 200 ml of dimethyl sulfoxide is treated with a solution of 23.4 g (0.2 mol) of indole in 100 ml of dimethyl sulfoxide. It is heated at 65° C. for 1 hour, then allowed to cool and 37.7 g (0.22 mol) of 4-nitrobenzyl chloride are then added dropwise. The solution is heated to 60° C., kept at room temperature for 14 hours and then poured into 700 ml of ater with stirring. The mixture is extracted in portions with a total of 300 ml of methylene chloride, the organic phase is dried using anhydrous sodium sulfate, filtered and the filtrate is concentrated in vacuo. The residue is purified on a silica gel column (silica gel 60, Merck AG, Darmstadt; eluent methylene chloride/ethanol 9:1, v/v).

Yield: 43.9 g (87% of theory); MS: m/e 253 (M+H).

2nd Stage

N-(Pyridin-4-yl)-[1-(4-nitrobenzyl)indol-3-yl]glyoxyl-amide (D-68836)

A solution of 4.50 ml of oxalyl chloride in 50 ml of ether is treated dropwise with a solution of 10.09 g (0.04 mol) of 1-(4-nitrobenzyl)indole in 50 ml of ether at OC [sic] and under a nitrogen atmosphere. The mixture is heated at reflux temperature for 2 hours and the solvent is then evaporated. 100 ml of tetrahydrofuran are added to the residue, it is cooled to –5° C. and a solution of of [sic] 9.32 g (0.099 mol) of 4-aminopyridine in 400 ml of tetrahydrofuran is added dropwise. The mixture is heated to reflux for 3 hours and allowed to stand at room temperature overnight. The 4-aminopyridine hydrochloride is filtered off with suction, the precipitate is washed with tetrahydrofuran, the filtrate is concentrated in vacuo and the residue is recrystallized from ethyl acetate.

Yield: 13.5 g (84% of theory); MS: m/e 401 (M+H).

3rd Stage

N-(Pyridin-4-yl)-[1-(4-aminobenzyl)indol-3-yl]glyoxyl-amide (D-68838)

A mixture of 200 mg of Raney nickel in 50 ml of dioxane is treated with a suspension of 320 mg (0.8 mmol) of N-(pyridin-4-yl)-[1-(4-nitrobenzyl)indol-3-yl]glyoxyl-amide in a solvent mixture of 150 ml of dioxane and 20 ml of isopropanol. Hydrogen is passed into this suspension with shaking at a gas pressure of 5 bar and the temperature is kept at 30–35° C. After about 3 hours, a further 400 mg of Raney nickel are added and the hydrogenation is continued at 35° C. and 5 bar for a further 8 hours with vigorous shaking. The catalyst is filtered off under an $N_2$ atmosphere, the filtrate is concentrated to dryness in vacuo and the residue is dried in vacuo at 40° C.

Yield: 273 mg (92% of theory); MS: m/e 371 (M+H).

Furthermore, the compounds of the general formula 1 with Z=O, R=$NO_2$ and $NH_2$ and $R_2$=aryl, aralkyl, heteroaryl, heteroaralkyl and the allylaminocarbonyl-2-methylprop-1-yl group can also be synthesized according to the synthesis route of Scheme 2:

Scheme 2

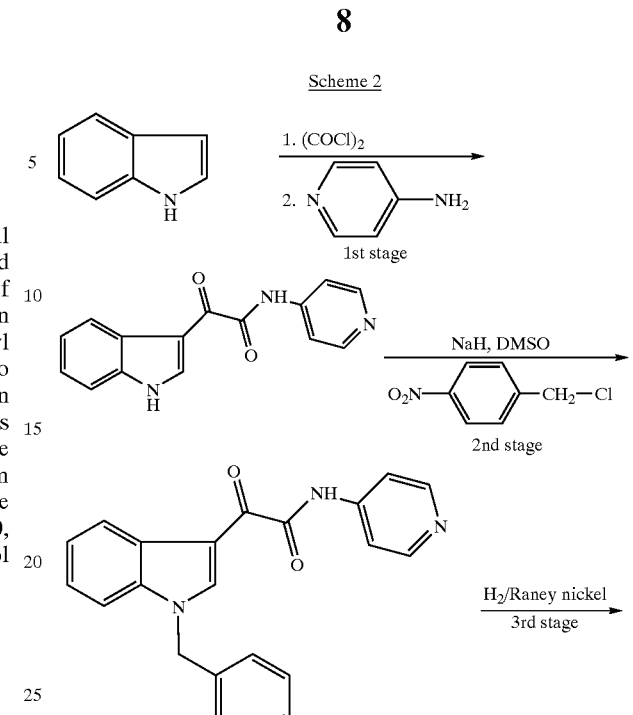

N-(Pyridin-4-yl)-[1-(4-aminobenzyl)indol-3-yl]glyoxl-amide

1st Stage

N-(Pyridin-4-yl)-(indol-3-yl)glyoxylamide

A solution of 10 g (85.3 mmol) of indole in 100 ml of ether is added dropwise at 0° C. to a solution of 9 ml of oxalyl chloride in 100 ml of anhydrous ether. The mixture is kept under reflux for 3 hours. A suspension of 12 g (127.9 mmol) of 4-aminopyridine in 500 ml of tetrahydrofuran is then added dropwise at –5° C., the reaction mixture is heated to reflux temperature with stirring for 3 hours and allowed to stand overnight at room temperature. It is filtered, the precipitate is treated with water and the dried compound is purified on a silica gel column (silica gel 60, Merck AG, Darmstadt) using the eluent methylene chloride/ethanol (10:1, v/v).

Yield: 9.8 g (43.3% of theory); MS: m/e 266 (M+H).

2nd Stage

N-(Pyridin-4-yl)-[1-(4-nitrobenzyl)indol-3-yl]glyoxylamide (D-68836)

The N-(pyridin-4-yl)-(indol-3-yl)glyoxylamide obtained according to the 1st Stage (Scheme 2) is reacted with 4-nitrobenzyl chloride according to the "benzylation procedure" (page 5) and the compound N-(pyridin-4-yl)-[1-(4-nitrobenzyl)indol-3-yl]glyoxylamide obtained is isolated.

Yield: 64% of theory; MS: mle 401 (M+H).

N-(Pyridin-4-yl)-[1-(4-aminobenzyl)indol-3-yl] glyoxylamide (D-68838)

The N-(pyridin-4-yl)-[1-(4-nitrobenzyl)indol-3-yl]-glyoxylamide obtained according to the 2nd Stage (Scheme 2) is catalytically hydrogenated according to the "hydrogenation procedure" (page 7) and the compound N-(pyridin-4-yl)-[1-(4-aminobenzyl)indol-3-yl]glyoxyl-amide obtained is isolated.

Yield: 94% of theory; MS: m/e 371 (M+H).

General Procedure for the Preparation of the Compounds of the General Formula 1 According to Scheme 2

1st Stage:

The indole derivative, which can be unsubstituted or substituted on C-2 or in the phenyl ring, dissolved in a solvent, as, for example, indicated above for oxalyl chloride, is added dropwise at a temperature between −5° C. and +5° C. to a solution prepared under a nitrogen atmosphere of a monomolar up to 60% excess amount of oxalyl chloride in an aprotic or nonpolar solvent, such as, for example, in diethyl ether, methyl tert-butyl ether, tetrahydrofuran, dioxane or alternatively dichloromethane. The reaction solution is then heated for 1 to 5 hours to a temperature between 10° C. and 120° C., preferably between 20° C. and 80° C., particularly between 30° C. and 60° C., and the solvent is then evaporated. The residue of the (indol-3-yl)glyoxyloyl chloride which remains is dissolved or suspended in an aprotic solvent, such as, for example, tetrahydrofuran, dioxane, diethyl ether, toluene or alternatively in a dipolar aprotic solvent, such as, for example, dimethylformamide, dimethylacetamide or dimethyl sulfoxide, cooled to a temperature between −10° C. and +10° C., preferably to −5° C. to 0° C., and treated in the presence of an acid scavenger with a solution of the primary or secondary amine in a diluent. Possible diluents are the solvents used for dissolving the "indolyl-3-glyoxyloyl chloride". Acid scavengers used are triethylamine, pyridine, dimethylaminopyridine, basic ion exchanger, sodium carbonate, potassium carbonate, powdered potassium hydroxide and excess primary or secondary amine employed for the reaction. The reaction takes place at a temperature from 0° C. to 120° C., preferably at 20–80° C., particularly between 40° C. and 60° C. After a reaction time of 1–4 hours and standing at room temperature for 24 hours, the mixture is filtered, the precipitate is digested with water, filtered off with suction and dried in vacuo. The desired compound is purified by recrystallization in an organic solvent or by column chromatography on silica gel or alumina. The eluent used is, for example, a mixture of dichloromethane and ethanol (10:1, vol/vol).

2nd Stage

The "indol-3-ylglyoxylamide" obtained according to the above procedure of the 1st Stage is dissolved in a protic, dipoplar aprotic or nonpolar organic solvent, such as, for example, in isopropanol, tetrahydrofuran, dimethyl sulfoxide, dimethylformamide, dimethyl-acetamide, N-methylpyrrolidone, dioxane, toluene or methylene chloride and added dropwise to a suspension of a base prepared in a three-necked flask under an $N_2$ atmosphere or employed in a molar amount or in excess, such as, for example, sodium hydride, powdered potassium hydroxide, potassium tert-butoxide, dimethylaminopyridine or sodium amide, in a suitable solvent. The desired alkyl, aralkyl or heteroaralkyl halide is then added either undiluted or in a diluent, which was also used, for example, for dissolving the "indol-3-ylglyoxylamide", if appropriate with addition of a catalyst, such as, for example, copper and the mixture is allowed to react for some time, e.g. for 30 minutes to 12 hours, and the temperature is kept within a range between 0° C. and 120° C., preferably between 30° C. and 80° C., particularly between 50° C. and 70° C. After completion of the reaction, the reaction mixture is added to water, the solution is extracted, for example, with diethyl ether, dichloromethane, chloroform, methyl tert-butyl ether, tetrahydrofuran or n-butanol and the organic phase obtained in each case is dried using anhydrous sodium sulfate. The organic phase is concentrated in vacuo, the residue which remains is crystallized by trituration or the oily residue is purified by distillation or by column or flash chromatography on silica gel or alumina. The eluent used is, for example, a mixture of methylene chloride and diethyl ether in the ratio 8:2 (vol/vol) or a mixture of methylene chloride and ethanol in the ratio 9:1 (v/v).

3rd Stage

The N-nitrobenzyl-substituted "indoleglyoxylamide obtained according to the above procedure (2nd stage) is dissolved in a protic solvent, such as, for example, methanol, ethanol, propanol or butanol or in a nonpolar solvent, such as, for example, tetrahydrofuran, dioxane or glycol dimethyl ether or in a dipolar aprotic solvent, such as, for example, dimethyl sulfoxide, dimethylformamide, dimethylacetamide or N-methylpyrrolidone and the solution is treated with a hydrogenation catalyst such as, for example, Raney nickel, palladium/carbon or platinum under a nitrogen atmosphere and with stirring. Hydrogen is passed into the suspension with moderate shaking at a gas pressure of 1–15 bar, preferably 2–10 bar, particularly at 4–6 bar and the temperature is raised to about 20°–80° C., preferably 30°–60° C., particularly to 45°–55° C. If appropriate, after about 1 hour a further amount of catalyst is added and the hydrogenation is continued. The hydrogenation was complete after a reaction time of 4–6 hours. The catalyst was filtered off under a nitrogen atmosphere, the solvent was concentrated to dryness and the colorless to yellowish residue was dried in vacuo at 40° C.

According to this general procedure for stages 1–3, on which the synthesis scheme 2 is based, the compounds D-68836 and D-68838 were synthesized, which have also already been prepared according to the synthesis procedure of reaction scheme 1.

It was possible to show the activity of the present compounds in a tubulin polymerization assay. In particular, proof was provided that D-68838 inhibits the polymerization of tubulin and thus exerts a destabilizing effect on microtubuli or the mitotic spindles.

What is claimed is:

1. A substituted N-benzylindol-3-ylglyoxylic acid derivative having antitumor action of the Formula 1

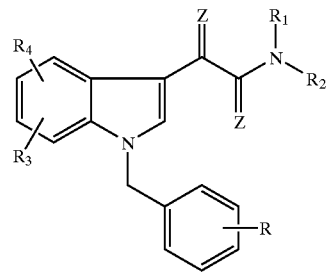

Formula 1 where

R is
nitro, amino, mono- or di($C_1$–$C_6$)-alkylamino, mono- or di ($C_1$–$C_6$)-cycloalkylamino, ($C_1$–$C_6$)-acylamino, phenyl ($C_1$–$C_6$)-alkylamino, aroylamino, ($C_1$–$C_6$)-alkylsulfonamido, arylsulfonamido, maleimido, succinimido, phthalimido, benzyloxycarbonylamino, tert-butoxycarbonylamino, 9-fluorenylmethoxy-carbonylamino, triphenylmethylamino, diphenylmethylsilylamino; or when $R_1$ is hydrogen, methyl, phenylmethyl group, benzyloxycarbonyl radical, tert-butoxycarbonyl radical or acetyl group, R is —NH—$CH_2$–COOH, —NH—CH($CH_3$) —COOH, ($CH_3$)$_2$CH—$CH_2$—$CH_2$—CH(NH)—COOH, $H_3$C—$CH_2$—CH($CH_3$)—CH(NH)—COOH, HOH$_2$C—CH(NH)—COOH, phenyl-$CH_2$—CH(NH)—COOH, HN=C($NH_2$)—NH—($CH_2$)$_3$—CH(NH)—COOH, $H_2$N—($CH_2$)$_4$—CH(NH)—COOH, $H_2$N—CO—$CH_2$—CH(NH)—COOH, or HOOC—($CH_2$)$_2$—CH(NH)—COOH;

wherein R radicals can alternatively be substituted on the carbon atoms 2, 3 and 4 of the phenyl ring;

$R_1$ is
hydrogen; ($C_1$–$C_6$)-alkyl, where the alkyl group are, optionally, mono- or polysubstituted with a phenyl ring, which is, optionally, mono- or polysubstituted with halogen, ($C_1$–$C_6$)-alkyl, ($C_3$–$C_7$)-cycloalkyl, carboxyl groups, carboxyl groups esterified with $C_1$–$C_6$-alkanols, trifluoromethyl groups, hydroxyl groups, methoxy groups, ethoxy groups, benzyloxy groups, or with a benzyl group which is mono- or polysubstituted in the phenyl moiety with ($C_1$–$C_6$)-alkyl groups, halogen atoms or trifluoromethyl groups; or
benzyloxycarbonyl group, tertiary-butoxycarbonyl radical, or acetyl group;

$R_2$ is a pyridine according to the formula 2

Formula 2

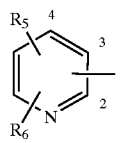

or its N-oxide, where the pyridine is alternatively bonded to the ring carbon atoms 2, 3 and 4 and is, optionally, substituted with substituents $R_5$ and $R_6$, where $R_5$ and $R_6$ are the same or different and are ($C_1$–$C_6$)-alkyl, ($C_3$–$C_7$)-cycloalkyl, ($C_1$–$C_6$)-alkoxy, nitro, amino, hydroxyl, halogen, trifluoromethyl, ethoxycarbonylamino radical and a ($C_1$–$C_4$)-carboxyalkyloxy I group;

$R_3$ and $R_4$ are the same or different and are hydrogen, ($C_1$–$C_6$)-alkyl, ($C_3$–$C_7$)-cycloalkyl, ($C_1$–$C_6$)-alkanoyl, ($C_1$–$C_6$)-alkoxy, halogen, benzyloxy, nitro, amino, ($C_1$–$C_4$)-mono- or dialkyl-substituted amino, ($C_1$–$C_6$)-alkoxycarbonylamino, or ($C_1$–$C_6$)-alkoxycarbonylamino-($C_1$–$C_6$)-alkyl group; and Z is O or S.

2. N-(Pyridin-4-yl)-[1-(4-aminobenzyl)indol-3-yl]-glyoxylamide.

3. N-(Pyridin-4-yl)- [1-(4-nitrobenzyl)indol-3-yl]-glyoxylamide.

4. Acid addition salts of the acid derivative according to any one of claims 1, 2 or 3, wherein said salts are salts of mineral acids, selected from hydrochloric acid, sulfuric acid, or phosphoric acid; salts of organic acids selected from acetic acid, lactic acid, malonic acid, maleic acid, fumaric acid, gluconic acid, glucuronic acid, citric acid, ascorbic acid, embonic acid, methanesulfonic acid, trifluoroacetic acid, succinic acid, 2-hydroxy-ethanesulfonic acid, nicotinic acid or p-toluene-sulfonic acid.

5. A pharmaceutical composition comprising an acid derivative according to any one of claims 1, 2 or 3, or its salt according to claim 4, with physiologically acceptable inorganic or organic acids and, optionally, pharmaceutically acceptable vehicles, diluents, excipients or mixtures thereof.

6. A pharmaceutical composition according to claim 5 in the form of tablets, coated tablets, capsules, solutions for infusion or ampoules, suppositories, patches, powder preparations suitable for use by inhalation, suspensions, creams and ointments.

7. An antitumor composition comprising an acid derivative of the Formula 1 according to claim 1.

8. A method of treatment of oncoses comprising administering to a patient in need of such treatment a pharmaceutical composition comprising an acid derivative of the Formula 1 according to claim 1.

9. A novel acid derivative of Formula 1 according to claim 1, wherein $R_2$ is unsubstituted pyridine.

10. A novel acid derivative of Formula 1 according to claim 1, wherein $R_1$, $R_3$ and $R_4$ are the same or different and are hydrogen or ($C_1$–$C_6$)-alkyl group.

* * * * *

UNITED STATES PATENT AND TRADEMARK OFFICE
CERTIFICATE OF CORRECTION

PATENT NO. : 6,432,987 B2
DATED : August 13, 2002
INVENTOR(S) : Gunther et al.

It is certified that error appears in the above-identified patent and that said Letters Patent is hereby corrected as shown below:

Title page,
Item [30], Foreign Application Priority Data, should read as follows:
-- [30]   Foreign Application Priority Data
Dec. 23, 1999   (DE)............................. 199 62 300.7 --

Column 7,
Line 15, please change "ater" to -- water --
Line 30, please change "OC [sic]" to -- 0° C --
Line 34, please change sentence from "cooled to -5° C. and a solution of of [sic] 9.32 g (0.099 mol)" to -- cooled to -5° C and a solution of 9.32 g (0.099 mol) --.

Column 9,
Line 1, please change "mle" to -- m/e --

Signed and Sealed this

Twenty-eighth Day of December, 2004

JON W. DUDAS
*Director of the United States Patent and Trademark Office*